(12) United States Patent
Foley et al.

(10) Patent No.: US 10,072,233 B2
(45) Date of Patent: Sep. 11, 2018

(54) FRAGRANCE AND FLAVOR COMPOSITIONS COMPRISING NEOPENTYL GLYCOL DIACETATE

(71) Applicant: P2 SCIENCE, INC., Woodbridge, CT (US)

(72) Inventors: Patrick Foley, New Haven, CT (US); Tania Salam, New Haven, CT (US); Yonghua Yang, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/655,374

(22) Filed: Jul. 20, 2017

(65) Prior Publication Data

US 2018/0037844 A1 Feb. 8, 2018

Related U.S. Application Data

(63) Continuation of application No. PCT/US2016/014557, filed on Jan. 22, 2016.

(60) Provisional application No. 62/181,480, filed on Jun. 18, 2015, provisional application No. 62/107,219, filed on Jan. 23, 2015.

(51) Int. Cl.

| | |
|---|---|
| *A61K 8/18* | (2006.01) |
| *A61Q 13/00* | (2006.01) |
| *C11B 9/00* | (2006.01) |
| *C09D 7/20* | (2018.01) |
| *C11D 3/20* | (2006.01) |
| *C11D 3/50* | (2006.01) |
| *A23L 33/10* | (2016.01) |
| *A23L 27/30* | (2016.01) |
| *A61K 8/37* | (2006.01) |
| *A61Q 19/00* | (2006.01) |
| *A61L 9/00* | (2006.01) |

(52) U.S. Cl.
CPC ............ *C11B 9/0019* (2013.01); *A23L 27/33* (2016.08); *A23L 33/10* (2016.08); *A61K 8/375* (2013.01); *A61L 9/00* (2013.01); *A61Q 13/00* (2013.01); *A61Q 19/00* (2013.01); *C09D 7/20* (2018.01); *C11D 3/2093* (2013.01); *C11D 3/50* (2013.01); *A23V 2002/00* (2013.01); *A61K 2800/10* (2013.01)

(58) Field of Classification Search
USPC ................................................ 512/26, 25, 1
See application file for complete search history.

(56) References Cited

U.S. PATENT DOCUMENTS

| | | | |
|---|---|---|---|
| 3,709,929 A | 1/1973 | Exner | |
| 4,017,537 A | 4/1977 | McCollum | |
| 4,368,145 A | 1/1983 | Licciardello | |
| 4,498,996 A * | 2/1985 | Klemarczyk | C11D 3/50 510/107 |
| 6,818,049 B1 * | 11/2004 | Schlosberg | C05G 3/0041 106/236 |

FOREIGN PATENT DOCUMENTS

| | | |
|---|---|---|
| JP | 55-136249 | 10/1980 |
| SU | 185341 | 10/1966 |
| WO | WO 1998/032728 | 7/1998 |
| WO | WO 1999/057217 | 11/1999 |
| WO | WO 2002/06487 | 1/2002 |
| WO | WO 2005/015158 | 2/2005 |

OTHER PUBLICATIONS

Abstract of Japanese Patent Application No. JP 55-136249 published Oct. 23, 1980.
CAS Registry Entry 13431-57-7, accessed Jul. 20, 2017, 1 page.
J. Coatings Tech. (1988), 60(759), 53-6.
J. Food Sci. (1989), 54(3), 770-3.

* cited by examiner

*Primary Examiner* — Jessica Whiteley
(74) *Attorney, Agent, or Firm* — Hoxie & Associates LLC

(57) ABSTRACT

The present application relates to the use of neopentyl glycol diacetate (CAS 13431-57-7) as a flavor and fragrance ingredient.

24 Claims, 2 Drawing Sheets

FRAGRANCE AND FLAVOR COMPOSITIONS COMPRISING NEOPENTYL GLYCOL DIACETATE

CROSS-REFERENCE TO RELATED APPLICATIONS

This application is a continuation application of International Application No. PCT/US2016/014557 filed on Jan. 22, 2016, which claims priority to, and the benefit of, U.S. Provisional Application No. 62/107,219, filed Jan. 23, 2015, and U.S. Provisional Application No. 62/181,480, filed Jun. 18, 2015, the contents of each of which are incorporated herein by reference in their entireties.

FIELD OF THE APPLICATION

The present application relates to the use of neopentyl glycol diacetate (CAS No. 13431-57-7) in flavor and fragrance compositions.

BACKGROUND

Scent is an important factor used to produce a sense of anticipation, quality, palatability, and security to many consumer products. Identifying effective aromas and flavors to impart in a product is an element that contributes to the success of the product, and is useful in product marketing, consumer satisfaction, and consumer retention. Sweet, resinous smells are particularly desirable fragrances and are often used in toiletries, cosmetics, household cleaners, room sprays, laundry, and fine fragrance applications, such as in perfumes and toilet waters. Similar flavors are also desirable in many dental hygiene products, orally administered medications, and food products.

Neopentyl glycol diacetate has been described in literature and characterized as useful in environmentally preferred fluids for industrial and process uses (U.S. Pat. No. 6,818,049 B1, WO 200206487 A1, WO 9957217 A1), in ester compositions for paints (WO 9832728 A1), in polysilicic compositions (HU 62623 A2, J. Coatings Tech. (1988), 60(759), 53-6), and as a volatile compound in curable coatings from Glassline packages (J. Food Sci. (1989), 54(3), 770-3).

Neopentyl glycol diacetate has not however been described and characterized as a compound that is useful in flavor and fragrance applications. This application describes the surprising and unexpected olfactive qualities of neopentyl glycol diacetate and its use as a readily accessible and cost effective fragrance and flavor ingredient, and potential applications thereof. This application further describes the use of neopentyl glycol diacetate as solvent, and potential applications thereof.

SUMMARY

In one aspect, the application relates to a fragrance composition comprising neopentyl glycol diacetate:

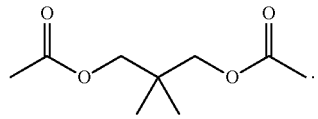

In another aspect, the application relates to a fragrance composition comprising neopentyl glycol diacetate and one or more additives, additional fragrance ingredients, or a combination of additives and fragrance ingredients.

In another aspect, the application relates to a flavor composition comprising neopentyl glycol diacetate

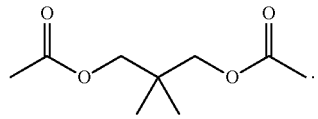

In another aspect, the application relates to a flavor composition comprising neopentyl glycol diacetate and one or more additives, additional flavor ingredients, or a combination of additives and flavor ingredients.

In another aspect, the application relates to various compositions comprising a solvent comprising neopentyl glycol diacetate.

The details of one or more embodiments of the application are set forth in the accompanying description below. Unless defined otherwise, all technical and scientific terms used herein have the same meaning as commonly understood by one of ordinary skill in the art to which this application belongs. In the case of conflict, the present specification will control.

Other features and advantages of the application will be apparent from the following detailed description, examples, and claims.

DETAILED DESCRIPTION

Figure 1:
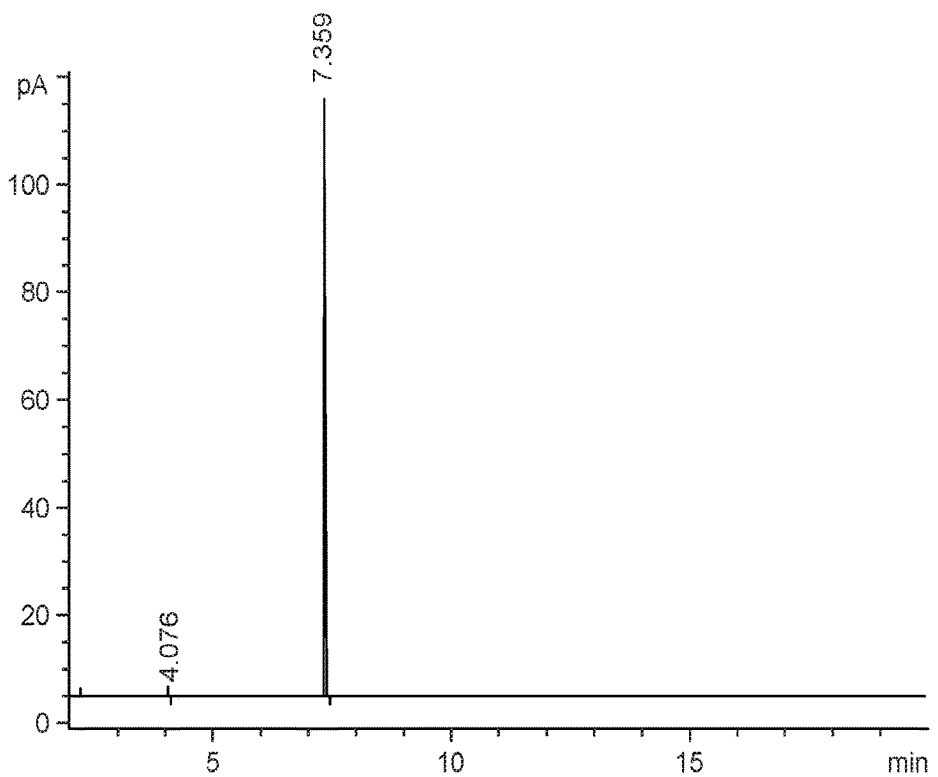
FIG. 1 is an analysis of purity of neopentyl glycol diacetate by GC-FID.

Neopentyl glycol diacetate has a unique aroma and flavor. It has thus been determined to be useful in imparting and providing desirable aromas and/or flavors to the products to which it is added. For example, neopentyl glycol diacetate may be used in any product where the inclusion of a pleasing fragrance or flavor is desired, including but not limited to, perfumes, household products, laundry products, personal care products, cosmetics, dental hygiene products, orally administered medications, and food products. Neopentyl glycol diacetate may be employed in varying amounts depending upon the specific fragrance or flavor product application, the nature and amount of other odor carrying ingredients present, and the desired aroma and/or flavor of the product.

Neopentyl glycol diacetate can be prepared by acetylation of neopentyl glycol, for example, with acetic anhydride or glacial acetic acid. An example preparation is show below:

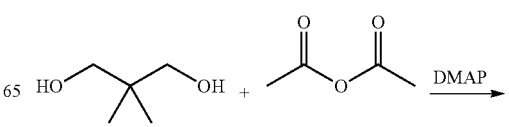

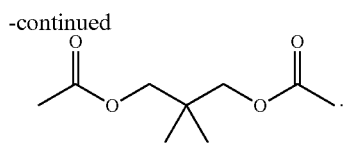

Neopentyl glycol diacetate may also be prepared by the condensation of neopentyl glycol with acetic acid, by acetylation of neopentyl glycol with acetyl chloride, or by any other method of acetylation.

The aroma of neopentyl glycol diacetate may be evaluated by testing the compound on a fragrance blotter, a small strip of paper used to sample the compound in aqueous form. Rather than smell a fragrance ingredient directly from the vial in which it is contained, fragrance blotters are used to provide a more accurate representation of the smell of a given fragrance ingredient. The aroma at the surface of a vial containing a fragrance ingredient is mostly comprised of the aroma's top notes, which are strong, but evaporate quickly. Use of a fragrance blotter therefore provides a better indication of the overall scent of neopentyl glycol diacetate, including its middle, and base notes, which makes up the majority of the odor experienced from an ingredient once it has been imparted in a product.

When neopentyl glycol diacetate is presented on a fragrance blotter in the absence of other fragrance ingredients (neat), it has an initial aroma that can be described as fresh, sweet, fruity, resinous, and myrrh-like, with notes of fattiness.

Furthermore, neopentyl glycol diacetate has a pleasing aromatic effect at a 10% dilution in triethylcitrate. The tenacity on the blotter, the aroma's ability to be detected over a given time period, is on the order of 5-10 hrs. Neopentyl glycol diacetate, neat or in solution, can thus be used in fragrance and flavor compositions to impart a sweet, fresh, pleasing aroma and/or flavor.

As used herein, the term "fragrance composition" means a mixture of fragrance ingredients, including auxiliary substances if desired, dissolved in a suitable solvent or mixed with a powdery substrate used to provide a desired odor to a product. Examples of products having fragrance compositions include, but are not limited to, perfumes, soaps, insect repellants and insecticides, detergents, household cleaning agents, air fresheners, room sprays, pomanders, candles, cosmetics, toilet waters, pre- and aftershave lotions, talcum powders, hair-care products, body deodorants, antiperspirants, and pet litter.

As used herein, the term "flavor composition" means a mixture of flavor ingredients, including auxiliary substances if desired, dissolved in a suitable solvent or mixed with a powdery substrate used to provide a desired flavor to a product. Examples of products having flavor compositions include, but are not limited to, dental hygiene products such as mouth wash, toothpaste, floss, and breath fresheners, orally administered medications including liquids, tablets or capsules, and food products.

Fragrance and flavor ingredients and mixtures of fragrance and flavor ingredients that may be used in combination with the disclosed compound for the manufacture of fragrance and flavor compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products. As used herein, the terms "fragrance ingredient" and "flavor ingredient" refer to ingredients other than neopentyl glycol diacetate. The application is directed to neopentyl glycol diacetate, also referred to herein as "the compound" of the present application, as a compound having desirable flavor and fragrance properties such that it may be considered for use as a novel flavor and fragrance ingredient. For clarity, neopentyl glycol is referred to by name or by "the compound" of the application to differentiate it from known fragrance and flavor ingredients used in flavor and fragrance compositions.

Examples of esters which may be used in the fragrance and flavor compositions of the present application include, but are not limited to, acrylic acid esters (methyl, ethyl, etc.), acetoacetic acid esters (methyl, ethyl, etc.), anisic acid esters (methyl, ethyl, etc.), benzoic acid esters (allyl, isoamyl, ethyl, geranyl, linalyl, phenylethyl, hexyl, cis-3-hexenyl, benzyl, methyl, etc.), anthranilic acid esters (cinnamyl, cis-3-hexenyl, methyl, ethyl, linalyl, isobutyl, etc.), N-methylanthranilic acid esters (methyl, ethyl, etc.), isovaleric acid esters (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), isobutyric acid esters (isoamyl, geranyl, citronellyl, terpenyl, cinnamyl, octyl, nellyl, phenylethyl, phenylpropyl, phenoxyethyl, butyl, propyl, isopropyl, hexyl, benzyl, methyl, ethyl, linalyl, rhodinyl, etc.), undecylenic acid esters (allyl, isoamyl, butyl, ethyl, methyl, etc.), octanoic acid esters (allyl, isoamyl, ethyl, octyl, hexyl, butyl, methyl, linalyl, etc.), octenoic acid esters (methyl, ethyl, etc.), octynecarboxylic acid esters (methyl, ethyl, etc.), caproic acid esters (allyl, amyl, isoamyl, methyl, ethyl, isobutyl, propyl, hexyl, cis-3-hexenyl, trans-2-hexenyl, linalyl, geranyl, cyclohexyl, etc.), hexenoic acid esters (methyl, ethyl, etc.), valeric acid esters (amyl, isopropyl, isobutyl, ethyl, cis-3-hexenyl, trans-2-hexenyl, cinnamyl, phenylethyl, methyl, etc.), formic acid esters (anisyl, isoamyl, isopropyl, ethyl, octyl, geranyl, citronellyl, cinnamyl, cyclohexyl, terpenyl, phenylethyl, butyl, propyl, hexyl, cis-3-hexenyl, benzyl, linalyl, rhodinyl, etc.), crotonic acid esters (isobutyl, ethyl, cyclohexyl, etc.), cinnamic acid esters (allyl, ethyl, methyl, isopropyl, propyl, 3-phenylpropyl, benzyl, cyclohexyl, methyl, etc.), succinic acid esters (monomenthyl, diethyl, dimethyl, etc.), acetic acid esters (anisyl, amyl, α-amylcinnamyl, isoamyl, isobutyl, isopropyl, isobornyl, isoeugenyl, eugenyl, 2-ethylbutyl, ethyl, 3-octyl, p-cresyl, o-cresyl, geranyl, α- or β-santalyl, cyclohexyl, cycloneryl, dihydrocuminyl, dimethyl benzyl carbinyl, cinnamyl, styralyl, decyl, dodecyl, terpenyl, guainyl, neryl, nonyl, phenyl ethyl, phenylpropyl, butyl, furfuryl, propyl, hexyl, cis-3-hexenyl, trans-2-hexenyl, cis-3-nonenyl, cis-6-noneyl, cis-3-cis-6-nonadienyl, 3-methyl-2-butenyl, heptyl, benzyl, bornyl, myrcenyl, dihydromyrcenyl, myrtenyl, methyl, 2-methylbutyl, menthyl, linalyl, rhodinyl, etc.), salicylic acid esters (allyl, isoamyl, phenyl, phenylethyl, benzyl, ethyl, methyl, etc.), cyclohexylalkanoic acid esters (ethyl cyclohexylacetate, allyl cyclohexylpropionate, allyl cyclohexylbutyrate, allyl cyclohexylhexanoate, allyl cyclohexyldecanoate, allyl cyclohexylvalerate, etc.), stearic acid esters (ethyl, propyl, butyl, etc.), sebacic acid esters (diethyl, dimethyl, etc.), decanoic acid esters (isoamyl, ethyl, butyl, methyl, etc.), dodecanoic acid esters (isoamyl, ethyl, butyl, etc.), lactic acid esters (isoamyl, ethyl, butyl, etc.), nonanoic acid esters (ethyl, phenylethyl, methyl, etc.), nonenoic acid esters (allyl, ethyl, methyl, etc.), hydroxyhexanoic acid esters (ethyl, methyl, etc.), phenylacetic acid esters (isoamyl, isobutyl, ethyl, geranyl, citronellyl, cis-3-hexenyl, methyl, etc.), phenoxyacetic acid esters (allyl, ethyl, methyl, etc.), furancarboxylic acid esters (ethyl furancarboxylate, methyl furancarboxylate, hexyl furancarboxylate, isobutyl furaneopentyl glycol diacetateropionate, etc.), propionic acid esters (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linallyl, terpenyl, α-methylpropionyl, β-methylpropionyl, etc.), heptanoic acid esters (allyl, ethyl, octyl, propyl, methyl, etc.), heptinecarboxylic acid esters (allyl, ethyl, propyl, methyl, etc.), myristic acid esters (isopropyl, ethyl, methyl, etc.), phenylglycidic acid esters (ethyl phenylglycidate, ethyl 3-methylphenylglycidate, ethyl p-methyl-β-phenylglycidate, etc.), 2-methylbutyric acid esters (methyl, ethyl, octyl, phenyl ethyl, butyl, hexyl, benzyl, etc.), 3-methylbutyric acid esters (methyl, ethyl, etc.), butyric acid esters (anisyl, amyl, allyl, isoamyl, methyl, ethyl, propyl, octyl, guainyl, linallyl, geranyl, cyclohexyl, citronellyl, cinnamyl, nellyl, terpenyl, phenylpropyl, β-phenylethyl, butyl, hexyl, cis-3-hexenyl, trans-2-hexenyl, benzyl, rhodinyl, etc.), and hydroxybutyric acid esters (methyl, ethyl, menthyl or the like of 3-hydroxybutyric acid esters).

Examples of alcohols that may be used in the fragrance and flavor compositions of the present application include, but are not limited to, aliphatic alcohols (isoamyl alcohol, 2-ethylhexanol, 1-octanol, 3-octanol, 1-octene-3-ol, 1-decanol, 1-dodecanol, 2,6-nonadienol, nonanol, 2-nonanol, cis-6-nonenol, trans-2, cis-6-nonadienol, cis-3, cis-6-nonadienol, butanol, hexanol, cis-3-hexenol, trans-2-hexenol, 1-undecanol, heptanol, 2-heptanol, 3-methyl-1-pentanol, etc.); terpene alcohols (borneol, isoborneol, carveol, geraniol, α- or β-santalol, citronellol, 4-thujanol, terpineol, 4-terpineol, nerol, myrcenol, myrtenol, dihydromyrcnol, tetrahydromyrcenol, nerolidol, hydroxycitronellol, farnesol, perilla alcohol, rhodinol, linalool, etc.); and aromatic alcohols (anisic alcohol, α-amylcinnamic alcohol, isopropylbenzylcarbinol, carvacrol, cumin alcohol, dimethylbenzylcarbinol, cinnamic alcohol, phenyl allyl alcohol, phenylethylcarbinol, β-phenylethyl alcohol, 3-phenylpropyl alcohol, benzyl alcohol, etc.).

Examples of aldehydes that may be used in the fragrance and flavor compositions of the present application include, but are not limited to, aliphatic aldehydes (acetaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.); aromatic aldehydes (anisic aldehyde, α-amylcinnamic aldehyde, α-methylcinnamic aldehyde, cyclamen aldehyde, p-isopropylphenylacetaldehyde, ethylvanillin, cumin aldehyde, salicylaldehyde, cinnamic aldehyde, o-, m- or p-tolylaldehyde, vanillin, piperonal, phenylacetaldehyde, heliotropin, benzaldehyde, 4-methyl-2-pheny-2-pentenal, p-methoxycinnamic aldehyde, p-methoxybenzaldehyde, etc.); and terpene aldehydes (geranial, citral, citronellal, α-sinensal, β-sinensal, perillaldehyde, hydroxycitronellal, tetrahydrocitral, myrtenal, cyclocitral, isocyclocitral, citronellyloxyacetaldehyde, neral, α-methylenecitronellal, myracaldehyde, vernaldehyde, safranal, etc.).

Examples of ketones which may be used in the fragrance and flavor compositions of the application include, but are not limited to, cyclic ketones (1-acetyl-3,3-dimethyl-1-cyclohexene, cis-jasmone, α-, β- or γ-irone, ethyl maltol, cyclotene, dihydronootkatone, 3,4-dimethyl-1,2-cyclopentadione, sotolon, α-, β-, γ- or δ-damascone, α-, β- or γ-damascenone, nootkatone, 2-sec-butylcyclohexanone, maltol, α-, β- or γ-ionone, α-, β- or γ-methylionone, α-, β- or γ-isomethylionone, furaneol, camphor, etc.); aromatic ketones (acetonaphthone, acetophenone, anisylideneacetone, raspberry ketone, p-methyl acetophenone, anisylacetone, p-methoxy acetophenone, etc.); and chain ketones (diacetyl, 2-nonanone, diacetyl, 2-heptanone, 2,3-heptanedione, 2-pentanone, methyl amyl ketone, methyl nonyl ketone, β-methyl naphthyl ketone, methyl heptanone, 3-heptanone, 4-heptanone, 3-octanone, 2,3-hexanedione, 2-undecanone, dimethyloctenone, 6-methyl-5-hepten-2-one, etc.).

Examples of acetals which may be used in the fragrance and flavor compositions of the present application include, but are not limited to, acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenylacetaldehyde dimethyl acetal, citronellyl methyl acetal, acetaldehyde phenylethylpropyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, Ambersage (manufactured by Givaudan), ethyl acetoacetate ethylene glycol acetal, and 2-phenylpropanal dimethyl acetal.

Examples of phenols which may be used in the fragrance and flavor compositions of the present application include, but are not limited to, eugenol, isoeugenol, 2-methoxy-4-vinylphenol, thymol, carvacrol, guaiacol, and chavicol, and vanillin.

Examples of ethers which may be used in the flavor and fragrance compositions of the present application include, but are not limited to, anethole, 1,4-cineole, dibenzyl ether, linalool oxide, limonene oxide, nerol oxide, rose oxide, methyl isoeugenol, methyl chavicol, isoamyl phenyl ethyl ether, β-naphtyl methyl ether, phenyl propyl ether, p-cresyl methyl ether, vanillyl butyl ether, α-terpinyl methyl ether, citronellyl ethyl ether, geranyl ethyl ether, rosefuran, theaspirane, decylmethyl ether, and methylphenyl methyl ether.

Examples of lactones which may be used in the flavor and fragrance compositions of the application include, but are not limited to, γ- or δ-decalactone, γ-heptalactone, γ-nonalactone, γ- or δ-hexylactone, γ- or δ-octalactone, γ- or δ-undecalactone, δ-dodecalactone, δ-2-decenolactone, methyl lactone, 5-hydroxy-8-undecenoic acid δ-lactone, jasmine lactone, menthalactone, dihydrocoumarin, octahydrocoumarin, and 6-methylcoumarin.

Examples of furans which may be used in the flavor and fragrance compositions of the present application include, but are not limited to, furan, 2-methylfuran, 3-methylfuran, 2-ethylfuran, 2,5-diethyltetrahydrofuran, 3-hydroxy-2-methyltetrahydrofuran, 2-(methoxymethyl)furan, 2,3-dihydrofuran, furfural, 5-methylfurfural, 3-(2-furyl)-2-methyl-2-propenal, 5-(hydroxymethyl)furfural, 2,5-dimethyl-4-hydroxy-3(2H)-furanone (furaneol), 4,5-dimethyl-3-hydroxy-2(5H)-furanone (sotolon), 2-ethyl-4-hydroxy-5- methyl-3(2H)-furanone (homofuraneol), 5-ethyl-3-hydroxy-4-methyl-2(5H)-furanone (homosotolon), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, and furfuryl acetate.

Examples of hydrocarbons which may be used in the flavor and fragrance compositions of the present application include, but are not limited to, α- or β-bisabolene, β-caryophyllene, p-cymene, terpinene, terpinolene, cadinene, cedrene, longifolene, farnesene, limonene, ocimene, myrcene, α- or β-pinene, 1,3,5-undecatriene and valencene.

Examples of acids that may be used in the flavor and fragrance compositions of the present application include, but are not limited to, geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, and cyclohexanecarboxylic acid.

The fragrance and flavor compositions of the application may comprise one or more natural extracts or oils including, but not limited to, anise, orange, lemon, lime, mandarin, petitgrain, bergamot, lemon balm, grapefruit, elemi, olibanum, lemongrass, neroli, marjoram, angelica root, star anise, basil, bay, calamus, chamomile, caraway, cardamom, cassia, cinnamon, pepper, perilla, cypress, oregano, cascarilla, ginger, parsley, pine needle, sage, hyssop, tea tree, mustard, horseradish, clary sage, clove, cognac, coriander, estragon, eucalyptus, fennel, guaiac wood, dill, cajuput, wormseed, pimento, juniper, fenugreek, garlic, laurel, mace, myrrh, nutmeg, spruce, geranium, citronella, lavender, lavandin, palmarosa, rose, rosemary, sandalwood, oakmoss, cedarwood, vetiver, linaloe, bois de rose, patchouli, labdanum, cumin, thyme, ylang ylang, birch, capsicum, celery, tolu balsam, genet, immortelle, benzoin, jasmine, cassie, tuberose, reseda, marigold, mimosa, opoponax, orris, vanilla and licorice. Each of these natural extracts or oils comprises a complex mixture of chemical compounds, which may include those compounds described above. Additional fragrance ingredients may be isolated from natural products, for example, geraniol and citronellal may be isolated from citronella oil, citral may be isolated from lemon-grass oil, eugenol may be isolated from clove oil, and linalool may be isolated from rosewood oil. Animal products used in fragrance compositions include, but are not limited to, musk, ambergris, civet and castoreum. The natural ingredients described herein may also be produced synthetically, and may include the compounds disclosed herein, and be used as fragrance and/or flavor ingredients in the fragrance and flavor compositions of the present application.

Examples of fragrance ingredients used in perfumes, air fresheners, laundry detergents, pet litters, cleaning products, liquid and bar soaps, shampoos and conditioners, cosmetics, deodorants, and personal hygiene products include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-isopropylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma, geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; and ethylene brassylate.

The fragrance and flavor ingredients in a given product's fragrance or flavor composition are selected based on the intended use of the product and the product's desired aroma. For example, flavor ingredients used in toothpaste, mouth wash, and dental hygiene products are selected to impart "freshness" and include, but are not limited to, spearmint oil, peppermint oil, star anise oil, lemon oil, and menthol.

Flavor compositions may be used to mask the unpleasant taste of orally administered medication. For example, if a medication is salty, a flavor composition that has cinnamon, raspberry, orange, maple, butterscotch, or *glycyrrhiza* (licorice) flavor may be used to mask the taste. If the medication is overly sweet, a flavor composition that has a berry, vanilla, or acacia flavor may render the medication more palatable. In the case of bitter tasting medication, flavor compositions that have cocoa, chocolate-mint, wild cherry, walnut, *glycyrrhiza* (licorice), and eriodictyon flavors might be used, whereas sour medications may be improved by flavor compositions that have fruity, citrus, or cherry flavors. These flavors may be provided by the natural or synthetic flavor ingredients discussed herein.

Examples of flavor ingredients used flavor compositions for food products include, but are not limited to, glucosyl steviol glycosides, isomenthols, carbonothoic acids, cassyrane, 1,5-octadien-3-ol, 2-mercaptoheptan-4-ol, 4 3-(methylthio)decanal, (4Z,7Z)-trideca-4,7-dienal, *persicaria odorata* oil, Amacha leaves extract, glutamyl-2-aminobutyric acid, glutamyl-2-aminobutyric acid, glutamyl-norvalyl-glycine, 0 glutamyl-norvaline, N1-(2,3-Dimethoxybenzyl)-N2-(2-(pyridin-2-yl)ethyl) oxalamide, 1-(2-hydroxy-4-methylcyclohexyl)ethanone, Mexican lime oil, Persian lime oil, 6-methoxy-2,6-dimethylheptanal, 3,5-undecadien-2-one, 2,5-undecadien-1-ol, triethylthialdine. 4-methylpentyl 4-methylvalerate, (R)-N-(1-methoxy-4-methylpentan-2-yl)-3,4-dimethylbenzamide, 2 N-acetyl glutamate, 1,3-propanediol, Szechuan pepper extract, *Tasmannia lanceolata* extract, *Mentha longifolia* oil, mangosteen distillate, ethyl 3-(2-hydroxyphenyl)propanoate, 1-cyclopropanemethyl-4-methoxybenzene, prenyl thioisobutyrate, prenyl thioisovalerate, matairesinol, stevioside, 1-(2,4-dihydroxyphenyl)-3-(3-hydroxy-4-methoxyphenyl)propan-1-one, Ethyl 5-formyloxydecanoate, 3-[3-(2-isopropyl-5-methyl-cyclohexyl)ureido]butyric acid ethyl ester, 2-Isopropyl-4-methyl-3-thiazoline, 2,6,10-trimethyl-9-undecenal, 5-mercapto-5-methyl-3-hexanone, Meyer lemon oil, teviol glycoside extract, *stevia rebaudiana*, rebaudioside A 60%, rubescenamine, 4-amino-5-(3-(isopropylamino)-2,2-dimethyl-3-oxopropoxy)-2-methylquinoline-3-carboxylic acid, 3-methyl-5-(2,2,3-trimethylcyclopent-3-en-1-yl)pent-4-en-2-ol, (1-Methyl-2-(1,2,2-trimethylbicyclo[3.1.0]hex-3-ylmethyl)cyclopropyl)methanol, erospicata oil, and curly mint oil. See L. J. Marnett et al., GRAS Flavoring Substances 26, Food Technology, 44-45 (2013).

In one aspect, a fragrance composition is provided comprising neopentyl glycol diacetate. In some embodiments, the fragrance composition may further comprise one or more additives, one or more fragrance ingredients, or a combination thereof.

In accordance with embodiments, a product is provided comprising a fragrance composition wherein the fragrance composition comprises neopentyl glycol diacetate. In some embodiments, the product may contain an additional substance, including but not limited to an excipient or a buffer.

In another aspect, a flavor composition is provided comprising neopentyl glycol diacetate. In some embodiments, the flavor composition may further comprise one or more additives, one or more flavor ingredients, or a combination thereof.

In accordance with embodiments, a product is provided comprising a flavor composition wherein the flavor composition comprises neopentyl glycol diacetate. In some embodiments, the product may contain an additional substance, including but not limited to an excipient or a buffer.

In accordance with embodiments, neopentyl glycol diacetate may be used as a solvent. Pleasant olfactory properties, low volatility, and excellent solubility make neopentyl glycol diacetate ideal for use as a solvent in products wherein a pleasing scent is desirable. For example, neopentyl glycol diacetate may be used as solvent alone, or in combination with other solvent materials, to provide a solvent for, e.g., cleaning compositions including cleaning sprays and industrial cleaners, air fresheners, degreasing compositions, detergent compositions, paint compositions, coating compositions, and other products that may benefit from a solvent comprising neopentyl glycol diacetate. Other solvent materials that may be used in a neopentyl glycol diacetate solvent system may include water-soluble organic solvents or oil-soluble organic solvents. Preferred solvents include, but are not limited to, triethyl citrate, triacetin, glycerol, ethanol, water, triglycerides, liquid waxes, propylene glycol derivatives, and ethylene glycol derivatives.

The amount of a given fragrance or flavor ingredient in a fragrance or flavor composition cannot be categorically described because it varies depending on the type product being scented or flavored, the intended use of the product, and the desired aroma and/or taste of the product. The amount of a fragrance or flavor ingredient in a fragrance or flavor composition is usually in the range of from about 1% to about 99% by mass of the fragrance composition. When the amount of the ingredient is too small, a sufficient strength of the scent or flavor may not be obtained. Further, when the amount of the ingredient is too large, a larger amount of the agent(s) needed to solubilize the ingredient may be needed, which may in turn reduce the desired aromatic or flavor properties of the end product by inhibiting volatilization or other mechanisms by which the flavor or fragrance is dispersed when the product is used or consumed. The amount of each of the fragrance and flavor ingredients in a given fragrance or flavor composition must therefore be selected based upon the aromatic and/or flavor characteristics of the selected ingredient, the overall composition of the product, and the intended aromatic and/or flavor effect.

Additives may be used in the flavor and fragrance compositions of the application. Additives that may be used include, but are not limited to, solvents and surfactants. Other fragrance and flavor composition additives will be selected in accordance with the intended use of the composition.

Solvents, for example water-soluble organic solvents, which may be used in the flavor and fragrance compositions of the application include, but are not limited to, ethanol, propanol, isopropanol, butanol, 3-methoxy-3-methyl-1-butanol, benzyl alcohol, ethyl carbitol (diethylene glycol monoethyl ether), ethylene glycol, propylene glycol, dipropylene glycol, butylene glycol, hexylene glycol, glycerin, ethylene glycol monomethyl ether, propylene glycol monomethyl ether, propylene glycol monoethyl ether, and dipropylene glycol monomethyl ether. These water-soluble solvents may be used solely or in combination. The content of the water-soluble organic solvent in the compositions of the application may be determined according to the desired composition properties, and is usually from about 1% to about 99% by mass. In one embodiment, the content of the water-soluble solvent is from about 1% to about 10% by mass, from about 5% to about 15% by mass, from about 10% to about 20% by mass, from about 15% to about 25% by mass, from about 20% to about 30% by mass, from about 25% to about 35% by mass, from about 30% to about 40% by mass, from about 35% to about 45% by mass, from about 40% to about 50% by mass, from about 45% to about 55% by mass, from about 50% to about 60% by mass, from about 55% to about 65% by mass, from about 60% to about 70% by mass, from about 75% to about 85% by mass, from about 80% to about 90% by mass, from about 85% to about 95% by mass, from about 90% to about 99% by mass, or from about 95% to about 99% by mass. In one embodiment, the content of the water-soluble solvent is 99% by mass, 98% by mass, 97% by mass, 96% by mass, 95% by mass, 94% by mass, 93% by mass, 92% by mass, 91% by mass, 90% by mass, 85% by mass, 80% by mass, 75% by mass, 70% by mass, 65% by mass, 60% by mass, 55% by mass, 50% by mass, 45% by mass, 40% by mass, 35% by mass, 30% by mass, 25% by mass, 20% by mass, 15% by mass, 10% by mass, 9% by mass, 8% by mass, 7% by mass, 6% by mass, 5% by mass, 4% by mass, 3% by mass, 2% by mass, or 1% by mass.

Oil-soluble organic solvents which may be used with the flavor and fragrance compositions of the application include, but are not limited to, isoparaffin, paraffin, limonene, pinene, triethyl citrate, benzyl benzoate, isopropyl myristate, triacetin, and silicon.

Preferred solvents include, but are not limited to, triethyl citrate, triacetin, glycerol, ethanol, water, triglycerides, liquid waxes, propylene glycol derivatives, and ethylene glycol derivatives.

The flavor and fragrance compositions of the present application may be used in combination with other substances, including, but not limited to, sequestering agents, preservatives, antioxidants, deodorizers, sterilization agents, ultraviolet absorbers, pH adjusters, insecticidal components, components for protection from insects, insect repellents, colorants, excipients, and buffers. The substances used in, or in addition to, the fragrance and flavor compositions of the present application may be determined by the product in which the composition is included. When the substance is used in a flavor or fragrance composition, it may be an additive. When the substance is used alongside a flavor or fragrance composition, it may be considered as part of a product composition that comprises a fragrance or flavor composition.

Excipients that may be used in the fragrance and flavoring compositions of the present application may vary depending on the use of the intended product and its overall composition. In some instances, the excipient may be included in the fragrance or flavor composition or may, alternatively, be independent of the composition. Excipients used in or with flavoring compositions of an orally administered medication include, but are not limited to, tablet coatings, such as a cellulose ether hydroxypropyl methylcellulose, synthetic polymer, shellac, corn protein zein or other polysaccharides, and gelatin. In pet litter, a solid excipient comprised of cellulosic or chlorophyll-containing agents or other materials may be used. In contrast, cosmetic excipients may include, but are not limited to, carbopol 940 ETD, triethanolamine, purified water, glycerine, imidazolidinyl urea, EDTA, 1polyvinyl alcohol, methyl parabenes phenoxyethanol 0, ethyl alcohol 1, peg 7 glyceryl cocoate, peg 6 triglyceryl caproic glycerides, acemulogar LAM V, isopropylmyristate, tegosoft CT, zantham gum, sepicide CL, polyquaternum 7, and Vaseline oils. Additional suitable excipients for use with or in a flavor and/or fragrance composition for a given product will be readily selected by those having ordinary skill in the art.

Buffers that may be used with the fragrance and flavoring compositions of the present application may vary depending on the use of the intended product and its overall composition. In some instances, the buffer may be included in the fragrance or flavor composition or may, alternatively, be independent of the composition. Examples of buffers that may be used in or with the fragrance and flavor compositions of the application include, but are not limited to, citrates, acetates, and phosphates. For example, trisodium citrate may be used as a flavor or as a preservative, and is known to impart tartness to a flavor, but also acts as a buffer. Trisodium citrate is an ingredient in a variety of sodas and other beverages, as well as drink mixes and bratwurst. In cosmetic products, disodium hydrogen phosphate, potassium dihydrogenphosphate, disodium hydrogenphosphate and, and citric acid may be used to buffer the pH of the product. In toothpaste, calcium carbonate and/or dicalcium phosphate may be used as pH buffers. Additional suitable buffers for use with or in a flavor and/or fragrance composition for a given product will be readily selected by those having ordinary skill in the art.

The fragrance and flavor compositions of the application may contain neopentyl glycol diacetate in a range of concentrations, for example, in one embodiment, from about 0.0005% to about 99.9% by mass neopentyl glycol diacetate with about 99.9995% to about 0.1% by mass of one or more additives and/or other fragrance or flavor ingredients. In one embodiment, a fragrance or flavor composition comprising about 0.5% to about 50% by mass neopentyl glycol diacetate may be combined with about 99.5% to about 50% by mass of one or more additives and/or other fragrance or flavor ingredients. In one embodiment, a fragrance or flavor composition comprising about 0.5% to about 10% by mass neopentyl glycol diacetate may be combined with about 99.5% to about 90% by mass of one or more additive and/or fragrance or flavor ingredients. In one embodiment, a fragrance or flavor composition comprising about 10% to about 20% by mass neopentyl glycol diacetate may be combined with about 90% to about 80% by mass of one or more additives and/or other fragrance or flavor ingredients. In one embodiment, a fragrance or flavor composition comprising about 20% to about 30% by mass neopentyl glycol diacetate may be combined with about 80% to about 70% by mass of one or more additives and/or other fragrance or flavor ingredients. In one embodiment, a fragrance or flavor composition comprising about 30% to about 40% by mass neopentyl glycol diacetate may be combined with about 70% to about 60% by mass of one or more additives and/or other fragrance or flavor ingredients. In one embodiment, a fragrance or flavor composition comprising about 40% to about 50% by mass neopentyl glycol diacetate may be combined with about 60% to about 50% by mass of one or more additives and/or other fragrance or flavor ingredients. In one embodiment, a fragrance or flavor composition comprising about 50% to about 60% by mass neopentyl glycol diacetate may be combined with about 50% to about 40% by mass of one or more additives and/or other fragrance or flavor ingredients. In one embodiment, a fragrance or flavor composition comprising about 60% to about 70% by mass neopentyl glycol diacetate may be combined with about 40% to about 30% by mass of one or more additives and/or other fragrance or flavor ingredients. In one embodiment, a fragrance or flavor composition comprising about 70% to about 80% by mass neopentyl glycol diacetate may be combined with about 30% to about 20% by mass of one or more additives and/or other fragrance or flavor ingredients. In one embodiment, a fragrance or flavor composition comprising about 80% to about 90% by mass neopentyl glycol diacetate may be combined with about 20% to about 10% by mass of one or more additives and/or other fragrance or flavor ingredients. In one embodiment, a fragrance or flavor composition comprising about 85% to about 95% by mass neopentyl glycol diacetate may be combined with about 15% to about 5% by mass of one or more additives and/or other fragrance or flavor ingredients. In one embodiment, a fragrance or flavor composition comprising about 90% to about 99.5% by mass neopentyl glycol diacetate may be combined with about 10% to about 0.5% by mass of one or more additives and/or other fragrance or flavor ingredients. In one embodiment, a fragrance or flavor composition comprising about 90% to about 98% by mass neopentyl glycol diacetate may be combined with about 10% to about 8% by mass of one or more additives and/or other fragrance or flavor ingredients. In one embodiment, a fragrance or flavor composition comprising about 90% to about 95% by mass neopentyl glycol diacetate may be combined with about 10% to about 5% by mass of one or more additives and/or other fragrance or flavor ingredients.

The function and advantages of these and other embodiments will be more fully understood from the following non-limiting examples. The examples are intended to be illustrative in nature and are not to be considered as limiting the scope of the embodiments discussed herein.

EXAMPLES

Example 1: Synthesis of Neopentyl Glycol Diacetate

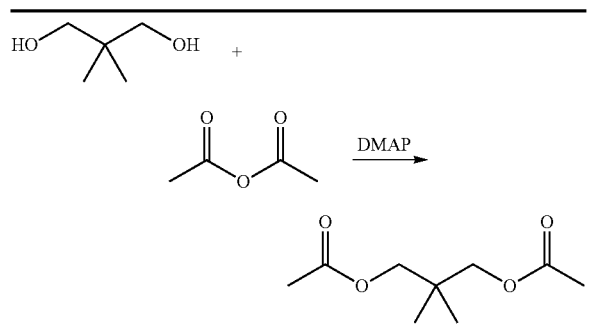

| Compound | MW | Mass/Volume | Moles |
|---|---|---|---|
| neopentyl glycol | 104.15 | 26.0 g | 0.25 |
| acetic anhydride | 102.09 | 57.3 g | 0.55 |
| N,N'-dimethylaminopyridine | 122.17 | 0.916 g | 0.0075 |
| tetrahydrofuran | | 100 ml | |

Acetic anhydride was slowly added over the course of 20 minutes to a stirring solution of neopentyl glycol (0.25 mol), N,N'-dimethylamino pyridine (0.0075 mol), and tertrahydrofuran (100 ml). Exotherm was observed. The reaction mixture was stirred overnight. GCMS revealed complete conversion of the starting material to the desired product. 20 ml of water was slowly added to the reaction mixture and then the mixture was placed on a rotary evaporator at reduced pressure to remove the tetrahydrofuran solvent. The resulting liquid was dissolved in ethyl acetate (200 ml), washed with 10% by wt. aqueous sodium carbonate solution (200 ml), followed by a wash with brine (200 ml). Ethyl Acetate was then removed on the rotary evaporator under reduced pressure to give 48 g of crude product. The crude product was then distilled at 1.27 mbar and 65° C. 3.3 g of product was collected in the first fraction, 14.5 g in the second fraction, and 14.6 g in the third fraction. The second and third fraction were found to have very high purity (>99% by GC-FID), sufficient for sensory evaluation. FIG. 1 shows the analysis of the purity of neopentyl glycol diacetate prepared by the method described herein.

The $^1$H NMR (400 MHz, CDCl$_3$) spectrum of neopentyl glycol diacetate prepared by the method described herein has chemical shift values (in ppm) for peaks at: δ 0.96 (d, J=0.8 Hz, 6H, —CH$_3$), 2.06 (m, J=0.8 Hz, 6H, —CH$_3$), 3.87 (s, 4H, —CH$_2$—).

Figure 2:
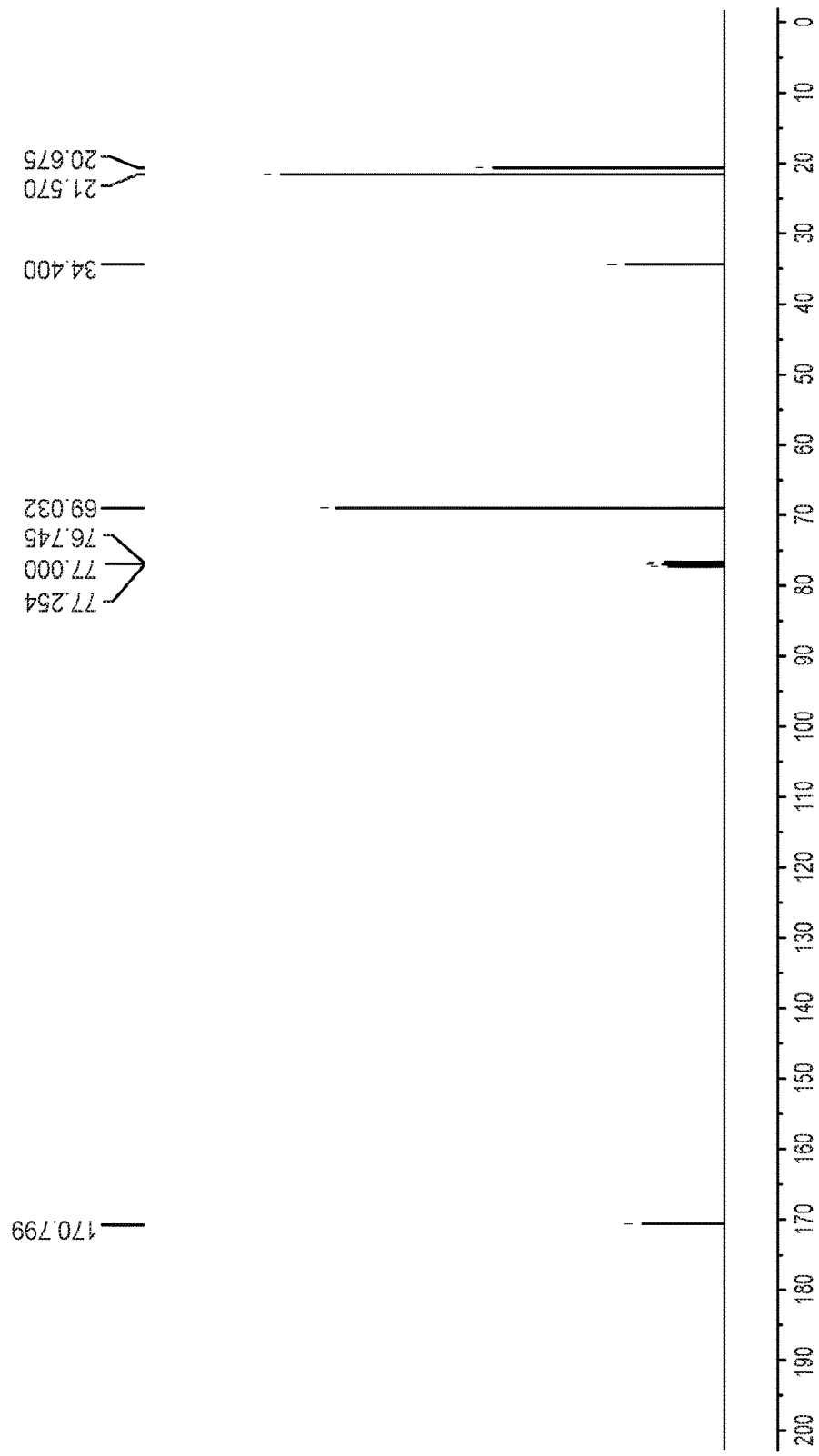
FIG. 2 is a $^{13}C$ NMR spectrum of neopentyl glycol diacetate.

FIG. 2 shows the $^{13}$C NMR (125 MHz, CDCl$_3$) spectrum of the neopentyl glycol diacetate, prepared by the method described herein. Chemical shift values (in ppm) for peaks in the spectrum are: δ 20.7 (2C, R—CH$_3$), 21.6 (2C, —CO—CH$_3$), 34.4 (1C, C), 69.0 (2C, C—CH2-O), and 170.8 (2C, —C=O).

Example 2: Calibration of Gas Chromatograph for Odor Detection

Odor detection thresholds may be determined using a gas chromatograph. The gas chromatograph is calibrated to allow determination of the exact volume of material injected by the syringe, the precise split ratio, and the hydrocarbon response using a hydrocarbon standard of known concentration and chain-length distribution. The air flow rate is measured and the sampled volume is calculated based on the assumed duration of a human inhalation of 12 seconds. Since the precise concentration at the detector at any point in time may be determined as described above, the mass per volume inhaled can be calculated, and hence, the concentration of material tested. To determine whether a material has a detectable odor threshold below 50 ppb, solutions are delivered to the sniff port at a concentration calculated using the method described above. Subsequently, a panelist sniffs the effluent from the gas chromatograph and identifies the retention time at which odor is noticed. Averaged data from all panelists yields the threshold of noticeability.

A calculated amount of analyte is injected onto the gas chromatograph column to achieve a 50 ppb concentration at the detector. Typical gas chromatograph parameters for determining odor detection thresholds via the method are listed below.

GC: 5890 Series II with FID detector
7673 Autosampler
Column: J&W Scientific DB-1
Length 30 meters ID 0.25 mm film thickness 1 micron
Method:
Split Injection: 17/1 split ratio
Autosampler: 1.13 microliters per injection
Column Flow: 1.10 mL/minute
Air Flow: 345 mL/minute
Inlet Temp. 245° C.
Detector Temp. 285° C.
Temperature Information
Initial Temperature: 50° C.
Rate: 5 C/minute
Final Temperature: 280° C.
Final Time: 6 minutes
Leading assumptions:
  (i) 12 seconds per sniff
  (ii) GC air adds to sample dilution

Example 3: Olfactory Analysis of Neopentyl Glycol Diacetate

Aqueous neopentyl glycol diacetate prepared by the method of Example 1 was sampled on a fragrance blotter to assess the compound's aroma.

Neopentyl glycol diacetate was first presented on a blotter neat. It was found to have an aroma that was sweet and described as fresh, fruity, resinous, and myrrh-like, with notes of fattiness.

A 10% dilution in triethylcitrate of neopentyl glycol diacetate synthesized by the method of Example 1 was then prepared and sampled on a blotter. The 10% dilution produced a similar, positive, aroma. The tenacity on the blotter was on the order of 5-10 hrs.

The olfactory analysis of neopentyl glycol diacetate demonstrated that the compound can be used to impart a desirable aroma to fragrance and flavor compositions.

Having now described some embodiments of the application, it should be apparent to those skilled in the art that the foregoing is merely illustrative and not limiting, having been presented by way of example only. The embodiments of the application can therefore be in other specific forms without departing from the spirit or essential characteristics thereof.

Those skilled in the art should recognize or be able to ascertain, using no more than routine experimentation, equivalents to the specific embodiments of the application. It is therefore to be understood that the embodiments described herein are presented by way of example only and that the scope of the application is thus indicated by the appended claims and equivalents thereto, and that the application may be practiced otherwise than as specifically described in the foregoing description.

The term "about," when used to describe one of the compositions of the application, refers to a recited percentage ±5%, ±4%, ±3%, ±2.5%, ±2%, ±1.5%, ±1%, ±0.75%, ±0.5%, ±0.25%, or ±0.1%. In one embodiment, the term "about," refers to a recited percentage ±5%. For example, "about 50%" refers to the range 45% to 55%. In one embodiment, the term "about," refers to a recited percentage ±2.5%. In one embodiment, the term "about," refers to a recited percentage ±1%. In one embodiment, the term "about," refers to a recited percentage ±0.5%. In one embodiment, the term "about," refers to a recited percentage ±0.1%.

As used herein, the singular forms "a," "an," and "the" include plural referents unless the context clearly dictates otherwise. Thus, for example, reference to "a fragrance ingredient" includes not only a single fragrance ingredient but also a combination or mixture of two or more different fragrance ingredients, reference to "an additive" includes a single additive as well as two or more additives, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

The entire disclosure of each of the patent documents and scientific articles referred to herein is incorporated by reference in its entirety for all purposes.

What is claimed:

1. A fragrance composition comprising neopentyl glycol diacetate.

2. The fragrance composition of claim 1, wherein the neopentyl glycol diacetate imparts a fragrance to the fragrance composition.

3. The fragrance composition of claim 2, further comprising one or more additives, one or more fragrance ingredients, or a combination thereof.

4. The fragrance composition of claim 3, wherein the fragrance composition comprises at least one additive.

5. The fragrance composition of claim 4, wherein the at least one additive comprises a surfactant.

6. The fragrance composition of claim 3, wherein the composition comprises at least one fragrance ingredient.

7. The fragrance composition of claim 6, wherein the at least one fragrance ingredient comprises an oil.

8. The fragrance composition of claim 2, wherein the fragrance composition comprises at least one additive and at least one fragrance ingredient.

9. A product composition comprising the fragrance composition according to claim 1, wherein the product composition is a perfume, air freshener, laundry detergent, household cleaning product, liquid or bar soap, shampoo, conditioner, hair spray, cosmetic, deodorant, insect repellant, insecticide, or pet litter composition.

10. The fragrance composition according to claim 1, wherein the concentration of neopentyl glycol diacetate is 0.0005% to 99.9% by mass.

11. A flavor composition comprising neopentyl glycol diacetate.

12. The flavor composition of claim 11, wherein the neopentyl glycol diacetate imparts a flavor to the flavor composition.

13. The flavor composition of claim 12, further comprising at least one additive, at least one flavor ingredient, or a combination of thereof.

14. The flavor composition of claim 13 comprising at least one additive.

15. The flavor composition of claim 14, wherein the at least one additive comprises a surfactant.

16. The flavor composition of claim 13 comprising at least one flavor ingredient.

17. The flavor composition of claim 16, wherein the at least one flavor ingredient comprises an oil.

18. The flavor composition of claim 13 comprising at least one additive and at least one flavor ingredient.

19. A product composition comprising the flavor composition according to claim 11, wherein the product composition is a toothpaste, mouthwash, orally administered medication, or food product composition.

20. The flavor composition according to claim 11, wherein the concentration of neopentyl glycol diacetate is 0.0005% to 99.9% by mass, 0.05% to 50% by mass, or 0.05% to 10% by mass.

21. The product composition according to claim 9, wherein the product composition is an air freshener composition.

22. The fragrance composition according to claim 1, wherein the composition is absent additional fragrance ingredients.

23. The fragrance composition according to claim 1, wherein the composition further comprises an oil-soluble organic solvent, and the fragrance composition comprises less than 10% by mass of water soluble solvent.

24. The fragrance composition according to claim 10, wherein the composition comprises from 20% to 50% by mass of neopentyl glycol diacetate.

* * * * *